United States Patent [19]

Le Peltier et al.

[11] Patent Number: 5,436,383

[45] Date of Patent: Jul. 25, 1995

[54] PROCESS FOR THE DEHYDROGENATION OF ALIPHATIC HYDROCARBONS SATURATED INTO OLEFINIC HYDROCARBONS

[75] Inventors: Fabienne Le Peltier; Sylvie Robert, both of Rueil Malmaison; Jean Paul Boitiaux, Poissy; Gerard Leger, Caluire; Jean Pierre Burzynski, Sainte Foy Les Lyon, all of France

[73] Assignee: Institut Francais du Petrole, Rueil Malmaison, France

[21] Appl. No.: 299,001

[22] Filed: Aug. 31, 1994

Related U.S. Application Data

[63] Continuation-in-part of Ser. No. 24,968, Mar. 2, 1993, abandoned.

[30] Foreign Application Priority Data

Mar. 2, 1992 [FR] France .................. 92 02570

[51] Int. Cl.$^6$ .................. C07C 5/327; C07C 5/333
[52] U.S. Cl. .................. 585/655; 585/658; 585/660; 585/661
[58] Field of Search .................. 585/655, 658, 660, 661

[56] References Cited

U.S. PATENT DOCUMENTS

| | | | |
|---|---|---|---|
| 3,456,026 | 7/1969 | Cohen | 260/669 |
| 3,468,969 | 9/1969 | Woerner | 260/680 |
| 3,998,900 | 12/1976 | Wilhelm | 260/668 D |
| 4,778,371 | 11/1988 | Imai et al. | 585/443 |
| 4,982,047 | 1/1991 | Barri et al. | 585/660 |
| 5,118,653 | 6/1992 | Barri et al. | 502/242 |
| 5,126,502 | 6/1992 | Barri et al. | 585/660 |
| 5,208,201 | 5/1993 | Barri et al. | 502/253 |
| 5,233,118 | 8/1993 | Bricker et al. | 585/660 |
| 5,304,694 | 4/1994 | Dessau et al. | 585/662 |
| 5,324,880 | 6/1994 | Dyroff | 585/660 |

FOREIGN PATENT DOCUMENTS

| | | |
|---|---|---|
| 568252 | 6/1958 | Belgium . |
| 1212491 | 3/1960 | France . |
| 1054623 | 4/1959 | Germany . |

*Primary Examiner*—Anthony McFarlane
*Assistant Examiner*—Nhat D. Phan
*Attorney, Agent, or Firm*—Millen, White, Zelano & Branigan

[57] ABSTRACT

Process for the dehydrogenation of a charge incorporating saturated aliphatic hydrocarbons essentially having 3 to 5 carbon atoms per molecule, in which the charge, previously heated to the reaction temperature and without premixing with the hydrogen, is introduced at the inlet of at least one reactor, where the dehydrogenation reaction is performed in the presence of a catalyst, preferably incorporating a support having at least one oxide of an element chosen from among the groups IIA, IIB, IIIA, IIIB, IVA and IVB of the periodic classification of elements, at least one noble metal from the platinum family, at least one promotor metal and at least one alkali metal or alkaline earth metal.

20 Claims, 1 Drawing Sheet

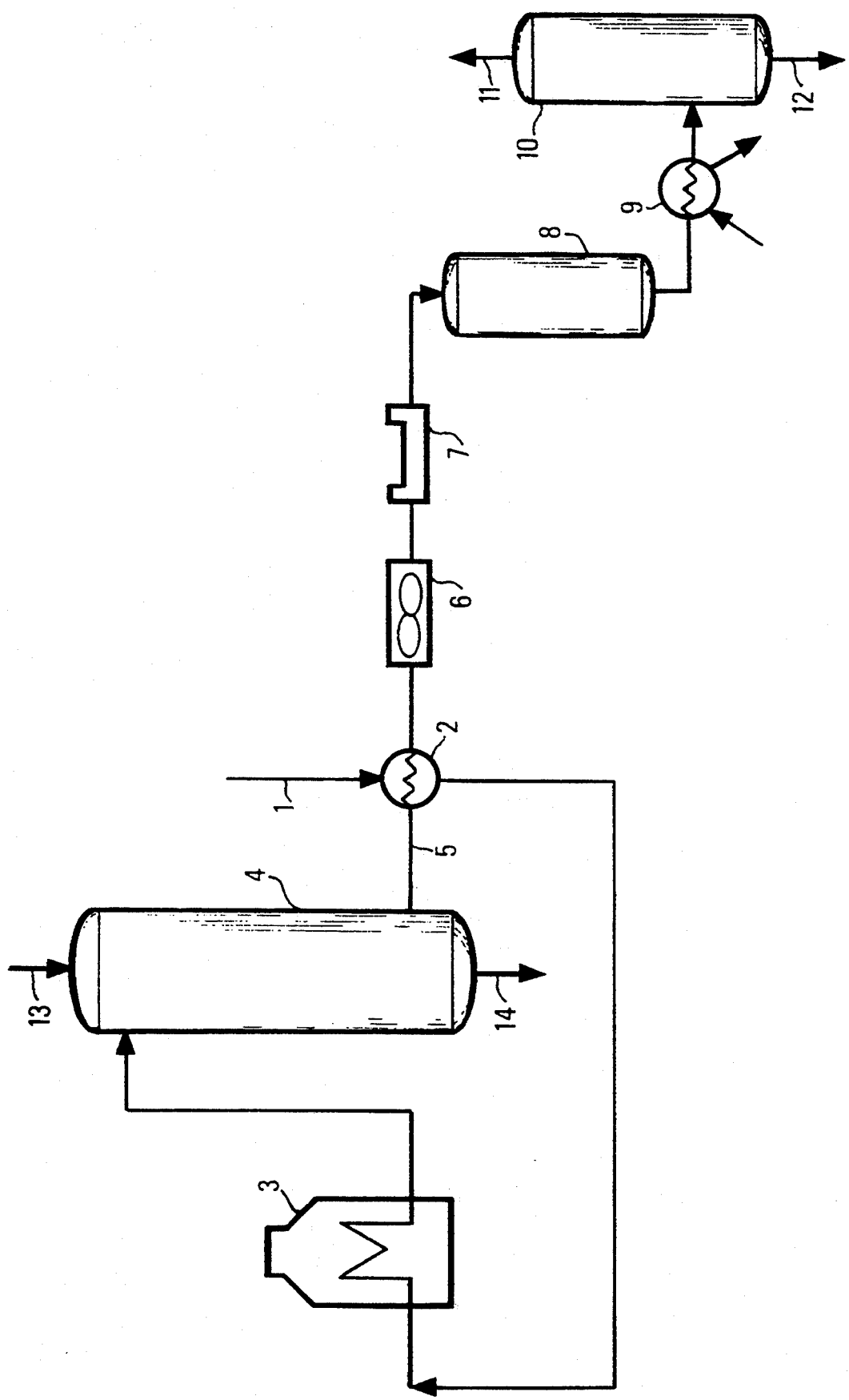

1

PROCESS FOR THE DEHYDROGENATION OF ALIPHATIC HYDROCARBONS SATURATED INTO OLEFINIC HYDROCARBONS

CROSS-REFERENCE TO RELATED APPLICATION

This application is a continuation-in-part of application Ser. No. 08/024,968, filed Mar. 2, 1993, which is hereby incorporated by reference, now abandoned.

BACKGROUND OF THE INVENTION

The present invention relates to a process for the dehydrogenation of light paraffins essentially having 3 to 5 carbon atoms per molecule and using an active catalyst for dehydrogenating the charge and which is characterized in that it is carried out without premixing the charge with hydrogen or diluent at the inlet of the reactor. It more particularly relates to the synthesis of isobutene, which is used for the preparation of MTBE (methyl tert.-butyl ether) with a view to improving the octane number in petrol.

It is of interest to vaporize aliphatic hydrocarbons with a low boiling point such as propanes, butanes, isobutanes, pentanes and isopentanes, which can be recovered following the extraction of the unsaturated products of $C_3$, $C_4$ and $C_5$ fractions from vapor-phase cracking or catalytic cracking, as well as LPG's or field gases. This justifies the interest attached to the performance of conversion processes for such hydrocarbons, which have high performance characteristics, are selective and economic, while also contributing to hydrogen formation.

The olefinic hydrocarbon production reaction has already been described, more particularly in U.S. Pat. No. 4,381,417 and U.S. Pat. No. 4,381,418, where use is made of platinum-based, supported metal catalysts. These patents describe a regenerative process in which there is a hydrogen injection in parallel to the hydrocarbon injection at the inlet of the reactor. Different solutions aiming at optimizing the recycling of the hydrogen-rich phase under the standpoint of thermal exchanges have been described. One of the major disadvantages is the need to recycle all or part of the hydrogen produced, which complicates the process diagram and increases costs.

Dehydrogenation reactions are very fast and reversible. The conversion rates are limited by the thermodynamic equilibrium conditions. The high temperatures and low partial pressures of hydrogen very favorably displace the reaction toward the formation of olefinic compounds. However, these severe conditions are very favorable to the formation of coke, which leads to the deactivation of the dehydrogenation catalysts. This is why the article, "Oleflex: C2-C5 dehydrogenation Updated," by B. V. Vora, P. R. Pujado and R. F. Anderson, Energy Progress, Vol. 6, No. 3, pp. 171-176 (1986), states that in order to maintain their stability, platinum-based catalysts are generally used in the presence of a hydrogen recycle, such as is described in U.S. Pat. No. 3,998,900. Other diluents can also be used, such as, e.g., water vapor, methane or ethane. However, U.S. Pat. No. 4,962,266 describes a process, preferably without hydrogen in the charge, which uses a catalyst incorporating platinum and a zincosilicalite. This patent refers to the low stability of a catalyst including platinum and chlorinated alumina.

SUMMARY OF THE INVENTION

The present invention relates to a dehydrogenation process based on a charge containing saturated aliphatic hydrocarbons essentially having 3 to 5, for example, 3 to 4, carbon atoms per molecule, said process being such that the charge, previously heated to the reaction temperature and without premixing with hydrogen or diluent, is introduced at the inlet of at least one reactor containing a catalyst in which the dehydrogenation reaction is performed. No significant amounts of hydrogen or diluents are introduced into the reactor during dehydrogenation. Preferably, no hydrogen or diluent is added during the dehydrogenation reaction. The catalyst comprises a support having at least one oxide of an element chosen from among groups IIA, IIB, IIIA, IIIB, IVA and IVB of the periodic classification of elements, at least one noble metal from the platinum family, at least one additional metal and at least one alkali metal or alkaline earth element.

The process according to the invention makes it possible to obtain a high conversion, a high selectivity of olefinic products and a good catalyst stability. Moreover, as no hydrogen is injected at the reactor inlet, it is possible to simplify the standard dehydrogenation process and therefore make it more economic.

The reactor can comprise a radial or axial gas flow fixed bed or a radial flow moving bed, as described in U.S. Pat. No. 4,277,444, or also a fluid bed. A gas flow moving bed, making it possible to renew the catalyst in operation, is preferred. In this case, a detailed description of the reactors is, e.g., given in U.S. Pat. No. 4,210,519 and means for ensuring the circulation of the catalyst between different reaction zones and the regeneration zone are, e.g., described in U.S. Pat. No. 4,981,575. Heating means can be positioned between the reactors, so that at the entrance of each of them the temperature conditions necessary for the reaction are ensured. The pressure in the reactors is kept as low as possible and compatible with the pressure drops of the lines, reactors and exchangers so as to take advantage of the thermodynamic equilibrium. In a first embodiment of the process, the effluent of the dehydrogenation reaction (constituted by unconverted aliphatic hydrocarbons and reaction products) is dried, e.g., by passing onto a fixed molecular sieve bed, and is then fed into a separator, where it is maintained under pressure and temperature conditions such that at the bottom a liquid phase is obtained incorporating unconverted hydrocarbons and the reaction products and at the head a hydrogen-rich gaseous phase. The drying conditions are generally a pressure of $3 \cdot 10^5$–$3 \cdot 10^6$ Pa, preferably $5 \cdot 10^5$–$10^6$ Pa and a temperature of 10°–100° C., preferably 30°–60° C. The separation conditions are normally a pressure of $2 \cdot 10^5$–$2 \cdot 10^6$ Pa, preferably $4 \cdot 10^5$–$8 \cdot 10^5$ Pa and a temperature of $-10°$–$-120°$ C., preferably $-30°$–$-80°$ C. The hydrogen produced can optionally be purified and used in situ or can be exported. In a second embodiment of the process, the effluent is compressed at a pressure of $2 \cdot 10^6$–$6 \cdot 10^6$ Pa and at a temperature of $-10°$ to $+20°$ C., which permits the separation of a gaseous phase incorporating hydrogen and a liquid phase incorporating the unconverted hydrocarbons and the reaction products. The gaseous phase can be purified or used as is.

Sulfur can be injected into the charge to minimize coking risks, due to the high temperature and the presence of olefins, of the materials from the reactors, lines and inter-reactor exchangers. The sulfur can, e.g., be injected in the form of organic sulfur such as dimethyl disulfide (DMDS) in quantities of 1-200 ppm based on the charge, for example, 56-70 ppm. Sulfur injection is not, however, preferred. Preferably, the dehydrogenation reaction is conducted in the absence of sulfur.

The dehydrogenation reaction generally takes place at a pressure of $2 \cdot 10^4$–$2 \cdot 10^6$ Pa and at a temperature of 400°–800° C., as a function of the nature of the charge. The temperature advantageously is 560°–700° C. for propane and 450°–600° C. for the fraction containing isobutane, under a preferred pressure of $10^5$–$3 \cdot 10^5$ Pa. The volume space velocity (based on the liquid charge) which is recommended is normally 0.5–20 $h^{-1}$, preferably 1.5–6 $h^{-1}$, especially 1.5–2.0 $h^{-1}$.

The catalyst used in the process according to the invention contains a support, at least one noble metal from the platinum family, at least one additional metal and at least one alkali metal or alkaline earth element. The supports are generally chosen from among oxides of elements selected from within the groups IIA, IIB, IIIA, IIIB, IVA and IVB of the periodic classification of elements such as, e.g., oxides of magnesium, aluminum, titanium, zirconium, thorium or silicon, taken singly or mixed with one another or mixed with oxides of other elements of the periodic classification. The preferred support is alumina. The specific surface of the support is advantageously 50–600 $m^2/g$, preferably 100–400 $m^2/g$. The noble metal is chosen from among elements of the group including platinum, palladium, ruthenium, rhodium, osmium and iridium. Platinum is the preferred element. The additional element is chosen from among elements of group VIIB and IVA, preferably rhenium, manganese, germanium, tin and lead. Tin is especially preferred. The alkali metal or alkaline earth element is preferably chosen from within the group formed by cesium, rubidium, potassium, sodium and lithium, preference being given to lithium or potassium. By weight based on an oxide support, the catalyst contains (a) 0.01–2% of at least one noble metal from the platinum family (b) 0.01–3% of at least one additional metal and (c) 0.1–3% of at least one alkali metal or alkaline earth element. The preferred catalytic formula contains 0.1–1% by weight platinum, 0.1–1.5% by weight tin and 0.1–1.5% by weight potassium. The catalyst can also contain 0.005–3.5% by weight of a halogen-containing compound such as chlorine. The catalyst can also contain 0.005–1% by weight sulfur.

The catalyst is generally prepared according to conventional methods consisting of impregnating the support by means of solutions of compounds of the metals to be introduced. Use is made either of a common solution of these metals, or separate solutions for the noble metal from the platinum family, for the additional metal and for the alkali metal or alkaline earth element. When using several solutions, it is possible to carry out intermediate drying and/or calcining operations. The final stage is normally a calcination, e.g., at 500°–800° C., preferably in the presence of oxygen, e.g., effectuated by an air sweep.

At least one additional metal from the tin group can be incorporated into the support by impregnating the support with the aid of an adequate aqueous solution containing at least one salt of the additional metal, e.g., in the form of chloride stannate, acetate or tartrate. The use of tin organic salts such as tartrate or acetate is preferred. At least one alkali metal or alkaline earth element can be introduced into the catalytic mass by means of an aqueous solution containing decomposable salts of at least one alkali metal or alkaline earth metal in the form of nitrate, carbonate or acetate. For example, very good results have been obtained using potassium carbonate. The introduction of at least one noble metal from the platinum family is preferably carried out by impregnating the support with an aqueous solution of at least one halogen-containing metallic compound. The platinum is generally introduced in the form of chloroplatinic acid. Following the introduction of the noble metal from the platinum family, the product obtained is dried and then calcined, preferably at a temperature of 400°–700° C., in the presence of at least one halogen-containing organic compound. Among the halogen-containing organic compounds reference can, e.g., be made to carbon tetrachloride, chloroform, dichloromethane and dichloropropane. Optionally, the catalyst can contain a sulfur compound. The sulfur can be introduced into the catalyst in numerous different ways, such as, e.g., in the presence of hydrogen sulfide diluted in hydrogen at a temperature of 400°–600° C.

The hydrocarbon charge can contain saturated hydrocarbons essentially having 3 to 5 carbon atoms per molecule. These hydrocarbons can be propane, n-butane, n-pentane, isomers of butane or pentane or mixtures thereof.

Preferably, the feed contains a major proportion of the component to be dehydrogenated (e.g., isobutane), preferably 40 vol. % or more, especially 50 vol. % or more.

BRIEF DESCRIPTION OF THE FIGURE

The attached drawing is a schematic flowsheet which illustrates the invention without limiting its scope, and is described hereinafter.

DETAILED DESCRIPTION OF FIGURE

The process according to the invention is generally performed in an apparatus incorporating a heat exchanger (2) making it possible to preheat the charge (1) by exchanging heat with the effluent (5) passing out of the final dehydrogenation reactor. The charge is then passed to a furnace (3), which permits the preheating thereof to the reaction temperature prior to injection into at least one reactor (4), where the endothermic dehydrogenation reaction is performed. Only one reactor is shown in the drawing, but the process according to the invention advantageously involves the use of several dehydrogenation reactors. These reactors are arranged in series, the effluent of one becoming the charge of the other. Inter-reactor furnaces permit the intermediate reheating of the effluent. Each reactor contains an annular catalyst bed moving slowly under the action of gravity, which makes it possible to renew the catalyst.

The fresh and/or regenerating catalyst is introduced by a supply pipe (13), while the spent catalyst is removed by a discharge pipe (14).

The dehydrogenation reaction effluent is then passed by the line (5) to the aforementioned charge/effluent heat exchanger (2) and then to the air cooler (6). The effluent is then fed into a compressor (7) and into a drier, e.g., a molecular sieve (8). After passing into an exchanger (9), the effluent is passed into a separator (10) making it possible to collect the hydrocarbons produced by a line (12) and a hydrogen-rich gas by a line (11). The hydrocarbons produced can then be fed into a fractionation section (not shown) for purification.

The following examples illustrate the invention without limiting the scope.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding French application 92/02.570, filed Mar. 2, 1992, are hereby incorporated by reference.

EXAMPLES

EXAMPLE 1

(Comparative)

In this example, 9.8 g of a catalyst, whose support is alumina and which contains 0.6% by weight platinum, 0.9% by weight tin, 0.9% by weight potassium and 1.5% by weight chlorine, was fed into an isothermal, tubular quartz reactor, which functions in falling flow manner at atmospheric pressure. The catalyst is calcined for 2 hours under a dry air flow of 15 l/h at 530° C. and with a temperature rise rate of 1° C. per minute. After scavenging under a nitrogen flow, the catalyst is then reduced at 530° C. under a hydrogen flow rate of 15 l/h for 2 hours. The reduction is ended under 15 l/h pure nitrogen at 530° C. for one hour. This is followed by the injection for 1 hour of 15 l/h of a mixture of hydrogen and hydrogen sulfide in a molar ratio of 100 and by the injection at a volume space velocity (based on the liquid charge) of 4 h$^{-1}$ of a hydrocarbon charge (HC), whose composition is given in Table 1.

TABLE 1

| Charge | % by weight |
|---|---|
| Propylene | 0.09 |
| Propane | 1.24 |
| Isobutane | 92.57 |
| Isobutene | 0.02 |
| n-butane | 6.00 |
| n-butenes | 0.05 |
| $C_5^+$ | 0.03 |

For a first period of 250 hours, there is a hydrogen injection in cocurrent with the hydrocarbon charge, so as to obtain a $H_2$/HC molar ratio at the reactor intake of 1. The catalyst is then very stable. As indicated in Table 2, there is virtually no evolution of the isobutene yield.

TABLE 2

| Time (h) | $H_2$/ $iC_4$ | T (°C.) | yield $iC_4$= (% by weight) | conversion $iC_4$ (% by weight) | selectivity $iC_4$= (% by weight) |
|---|---|---|---|---|---|
| 50 | 1 | 540 | 31.3 | 36.6 | 85.6 |
| 248 | 1 | 540 | 31.2 | 34.4 | 90.7 |

EXAMPLE 2

(According to the Invention)

In this example, the catalyst is accurately tested under the same conditions as in the preceding example, but according to the invention the charge is introduced into the reactor without premixing with the hydrogen. Also, a mixture of hydrogen and hydrogen sulfide is not injected during and after the injection of the hydrocarbon charge. A high conversion is obtained at a temperature lower by 30° C. than that in Example 1 (510° C. instead of 540° C.). In addition, despite the severe conditions ($H_2$/$iC_4$=0), the catalyst remains stable for a further period of 150 hours.

TABLE 3

| Time (h) | $H_2$/ $iC_4$ | T (°C.) | yield $iC_4$= (% by weight) | conversion $iC_4$ (% by weight) | selectivity $iC_4$= (% by weight) |
|---|---|---|---|---|---|
| 0 | 0 | 510 | 38.1 | 41.4 | 92.1 |
| 50 | 0 | 510 | 37.9 | 40.3 | 94.0 |
| 100 | 0 | 510 | 36.2 | 38.6 | 93.7 |
| 150 | 0 | 510 | 36.4 | 38.4 | 94.8 |
| 250 | 0 | 510 | 36.1 | 37.9 | 95.2 |

EXAMPLE 3

(Comparative)

In this example, 9.8 g of a catalyst, whose support is alumina and which contains 0.6% by weight platinum, 0.9% by weight tin, 0.9% by weight potassium and 1.5% by weight chlorine, was fed into an isothermal, tubular quartz reactor, which functions in falling flow manner at atmospheric pressure. The catalyst is calcined for 2 hours under a dry air flow of 15 l/h at 530° C. and with a temperature rise rate of 1° C. per minute. After scavenging under a nitrogen flow, the catalyst is then reduced at 530° C. under a hydrogen flow rate of 15 l/h for 2 hours. The reduction is ended under 15 l/h pure nitrogen at 530° C. for one hour. This is followed by the injection for 1 hour of 15 l/h of a mixture of hydrogen and hydrogen sulfide in a molar ratio of 100 and the injection at a volume space velocity (based on the liquid charge) of 2.6 h$^{-1}$ of a hydrocarbon charge (HC), whose composition is given in Table 4.

TABLE 4

| Charge | % by weight |
|---|---|
| Propylene | 0.09 |
| Propane | 1.24 |
| Isobutane | 92.57 |
| Isobutene | 0.02 |
| n-butane | 6.00 |
| n-butenes | 0.05 |
| $C_5^+$ | 0.03 |

For a first period of 250 hours, there is a hydrogen injection in cocurrent with the hydrocarbon charge, so as to obtain a $H_2$/HC molar ratio at the reactor intake of 1. The catalyst is then very stable. As indicated in Table 5, there is virtually no evolution of the isobutene yield.

TABLE 3

| Time (h) | $H_2$/ $iC_4$ | T (°C.) | yield $iC_4$= (% by weight) | conversion $iC_4$ (% by weight) | selectivity $iC_4$= (% by weight) |
|---|---|---|---|---|---|
| 50 | 1 | 565 | 38 | 41 | 93 |
| 100 | 1 | 565 | 35 | 37 | 94 |
| 150 | 1 | 565 | 34 | 36 | 94 |

The following table lists the productivity of Examples 1-3:

TABLE 6

| Example | Productivity (feed transformed iC$_4$= (g)/catalyst (g)/h) |
| --- | --- |
| 1 | 158 |
| 2 | 187 |
| 3 | 105 |

All of the above examples are performed using a fixed catalyst bed.

In Examples 1 and 2, the process was conducted at different temperatures in an attempt to achieve the same level of conversion of isobutane (iC$_4$) while using different H$_2$/iC$_4$ ratios (1 and 0 for, respectively, Examples 1 and 2). The conversion levels are not, however, the same; conversion in Example 2 is greater than that of Example 1. Still, the results demonstrate advantages of the process according to the invention. For example, in Example 2, the iC$_4$ conversion is higher at a lower temperature, i.e., 510° C. versus 540° C., and without addition of H$_2$ or a diluent. In addition, the selectivity of iC$_4$= is higher in Example 2, particularly at the beginning of the reaction. Since, as shown in Example 2, lower process temperatures can be used, the addition of sulfur during the reaction for purposes of preventing corrosion is unnecessary. Furthermore, in a regenerative bed process, the duration of the cycle and thus the catalyst residence time can be longer since, due to the lower working temperature, addition of sulfur is not needed.

In Example 3, the initial level of iC$_4$ conversion is comparable to that of Example 2. However, at 150 hours, the iC$_4$ conversion decreases to 36% and the yield decreases to 34%. This indicates a quicker deactivation of the catalyst. Although the volume space velocity of Example 3 is 2.6 h$^{-1}$, whereas in Example 2 it is 4.0 h$^{-1}$, one skilled in the art would recognize that catalyst deactivation would be even faster at a higher volume space velocity. Alternatively, one skilled in the art would recognize that the catalyst stability in Example 2 would be greater at a lower volume space velocity, e.g., 2 h$^{-1}$ or lower.

Also, Examples 1 and 3 inject a hydrogen and hydrogen sulfide mixture during and after the injection of the hydrocarbon charge. However, no such H$_2$/H$_2$S injection is used in Example 2. It is believed that the introduction of sulfur without providing for the introduction of H$_2$ would lead to quicker deactivation of the catalyst.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the dehydrogenation of a charge consisting essentially of saturated aliphatic hydrocarbons having 3-5 carbon atoms per molecule, comprising:
    introducing said charge, previously heated to reaction temperature, into the inlet of at least one reactor containing dehydrogenation catalyst and performing a dehydrogenation reaction in said at least one reactor in the presence of said dehydrogenation catalyst,
    wherein, during said dehydrogenation reaction, neither hydrogen nor a diluent is introduced into said at least one reactor, and
    said dehydrogenation catalyst comprises a support of alumina supporting at least one noble metal from the platinum family, at least one additional metal from group IVA or VIIB of the periodic classification of the elements and at least one alkali metal or alkaline earth metal.

2. A process according to claim 1, wherein said catalyst contains, by weight based on the support, 0.01-2% of at least one noble metal from the platinum family, 0.01-3% of at least one additional metal and 0.1-3% of at least one alkali metal or alkaline earth metal.

3. A process according to claim 1, wherein said noble metal is platinum, said at least one additional metal is tin and said alkali metal or alkaline earth metal is lithium or potassium.

4. A process according to claim 1, wherein said catalyst contains 0.1-1% by weight platinum, 0.1-1.5% by weight tin and 0.1-1.5% by weight potassium.

5. A process according to claim 1, wherein said catalyst further contains at least one halogen-containing compound.

6. A process according to claim 1, wherein said dehydrogenation reaction is performed at a pressure of 2·10$^4$–2·10$^6$ Pa, at a temperature of 400°–800° C. and a volumetric space velocity, based on the liquid charge, of 0.5-20 h$^{-1}$.

7. A process according to claim 1, wherein effluent from said at least one reactor is dried and then fed into a separator, from which a liquid phase, containing unconverted hydrocarbons and reaction products, and a hydrogen-rich gaseous phase are obtained.

8. A process according to claim 1, wherein effluent from said at least one reactor is compressed, whereby a liquid phase, containing unconverted hydrocarbons and reaction products, and a hydrogen-rich gaseous phase are obtained.

9. A process according to claim 1, wherein said charge contains 40 vol. % or more of the component to be dehydrogenated.

10. A process according to claim 4, wherein said charge contains 40 vol. % or more of the component to be dehydrogenated.

11. A process according to claim 9, wherein said component is isobutane.

12. A process according to claim 10, wherein said catalyst further contains at least one halogen-containing compound.

13. A process according to claim 12, wherein said dehydrogenation reaction is performed at a pressure of 2·10$^4$–2·10$^6$ Pa, at a temperature of 400°–800° C. and a volumetric space velocity, based on the liquid charge, of 0.5-20 h$^{-1}$.

14. A process according to claim 1, wherein said dehydrogenation reaction is conducted in the presence of a moving catalyst bed.

15. A process according to claim 14, wherein the catalyst residence time in said reactor is greater than 100 hours.

16. A process according to claim 14, wherein the catalyst residence time in said reactor is greater than 150 hours.

17. A process according to claim 14, wherein the catalyst residence time in said reactor is greater than 250 hours.

18. A process according to claim 1, wherein said dehydrogenation reaction is carried out in the presence of a fixed catalyst bed.

19. A process according to claim 1, wherein sulfur is not introduced into the reactor during the dehydrogenation reaction.

20. A process for the dehydrogenation of a charge consisting essentially of saturated aliphatic hydrocarbons having 3–5 carbon atoms per molecule, comprising:

introducing said charge, previously heated to reaction temperature, into the inlet of at least one reactor containing dehydrogenation catalyst and performing a dehydrogenation reaction in said at least one reactor in the presence of said dehydrogenation catalyst, wherein no hydrogen, diluent or sulfur is introduced into said at least one reactor during said dehydrogenation reaction, and said dehydrogenation catalyst comprises a support of alumina supporting at least one noble metal from the platinum family, at least one additional metal from group IVA or VIIB of the periodic classification of the elements and at least one alkali metal or alkaline earth metal.

* * * * *